United States Patent [19]

Ellis, Jr. et al.

[11] Patent Number: 4,970,348

[45] Date of Patent: Nov. 13, 1990

[54] CHROMIUM HALOGENATED COORDINATION COMPLEXES FOR THE OXIDATION OF BUTANE TO METHYLETHYLKETONE

[75] Inventors: Paul E. Ellis, Jr., Downingtown; James E. Lyons, Wallingford, both of Pa.

[73] Assignee: Sun Refining and Marketing Company, Philadelphia, Pa.

[21] Appl. No.: 432,266

[22] Filed: Nov. 6, 1989

[51] Int. Cl.$^5$ ............................................. C07C 45/33
[52] U.S. Cl. .................................................. 568/399
[58] Field of Search ........................ 568/320, 360, 399

[56] References Cited

U.S. PATENT DOCUMENTS

| | | |
|---|---|---|
| 3,816,548 | 6/1974 | Williams et al. ..................... 568/399 |
| 3,825,605 | 7/1974 | Johnson .............................. 568/399 |
| 4,028,423 | 6/1977 | Brownstein et al. ............... 568/399 |
| 4,038,322 | 7/1977 | de Radzitzky et al. ............ 568/399 |
| 4,803,187 | 2/1989 | Lyons et al. ........................ 568/399 |
| 4,839,323 | 6/1989 | Goe et al. ........................... 568/320 |

OTHER PUBLICATIONS

Chang et al., J. Chem. Comm. (1981) pp. 778-90.
Adler et al., J. Inorg., Nucl. Chem., vol. 32 p. 2443 (1970).

*Primary Examiner*—James H. Reamer
*Attorney, Agent, or Firm*—J. Edward Hess; Donald R. Johnson; Q. Todd Dickinson

[57] ABSTRACT

Butane is selectively oxidized to methylethylketone with a chromium-halogenated ligand coordination complex catalyst.

5 Claims, No Drawings

CHROMIUM HALOGENATED COORDINATION COMPLEXES FOR THE OXIDATION OF BUTANE TO METHYLETHYLKETONE

BACKGROUND OF THE INVENTION

This application is a continuation in part of U.S. application Ser. No. (S-86-002 CIP-2), which is a continuation-in-part of U.S. application Ser. No. 066,666, filed June 26, 1987, which is a continuation-in-part of U.S. application Ser. No. 246, filed Jan. 2, 1987, both applications filed in the name of Paul E. Ellis, Jr., James E. Lyons, and Harry K. Myers, Jr.

This invention relates to a process for the catalytic oxidation of butane to methylethylketone (MEK) with air or oxygen. The catalyst is a halogenated porphyrin complex of chromium.

MEK is a solvent widely used in the petroleum and chemical industries. It is now made from butene by hydration to sec-butyl alcohol followed by oxidation of the alcohol to MEK. A superior method of making MEK would be by the direct air oxidation of butane since the latter is also available in the petroleum industry, indeed it is in oversupply. However, this method has been extremely difficult to achieve and has never been practiced successfully on a commercial scale.

We have now discovered what we believe is the first example of a highly selective process for the air oxidation of butane to MEK. For the purpose of this application the term air also includes oxygen per se.

SUMMARY OF THE INVENTION

In accordance with the present invention, it has now been found that butane can readily be oxidized to MEK with air with the production of only minor amounts of by-products when the catalyst is a halogenated porphyrin coordination complex of chromium. Whereas most transition metals in metal-containing halogenated porphyrin coordination complexes provide a catalyst which is highly selective for the formation of alcohols, chromium appears to be unique in providing high selectivity to ketones, at least when the chargestock is butane. What by-products are formed are useful chemicals as sec-butyl alcohol and acetic acid with almost no formation of carbon oxides.

Our oxidation of butane to MEK, which may be carried out in a generally known manner, is desirably conducted in the liquid phase, although this is not critical either neat or using such organic solvents as benzene, acetonitrile, methyl acetate, or like solvents which are inert to the conditions of the reactions. The pressure will range from about 15 to 3000 psig, preferably 30 to 1000 psig, and the temperature should be from about 25° to 250° C., more preferably 100° to 170° C. If a solvent is employed, the butane is dissolved in or bubbled through the solvent, together with air or oxygen, in the presence of the aforementioned chromium coordination complex catalyst, for periods of time sufficient to yield the desired oxidation product, generally from about 0.5 to 100 hours, and more preferably from 1 to 10 hours.

The choice of solvent, while not critical, can have an effect on the rates and selectivities obtained and should be selected carefully in order to optimize the desired results. Thus, by routine experimentation the optimum solvent for the particular process conditions can readily be determined.

The ratios of the various reactants may vary widely, and are not critical. For example, the amount of catalyst employed can range from about $10^{-6}$ to $10^{-3}$ moles per mole of butane, and more preferably from about $10^{-5}$ to $10^{-4}$ moles of catalyst per mole of butane, although other amounts are not precluded; while the amount of oxygen relative to the hydrocarbon starting material may also vary widely, generally $10^{-2}$ to $10^2$ moles of oxygen per mole of butane. Care should be taken since some of the ratios fall within explosive limits. The catalysts used in our invention are almost always soluble unless used in large excess. Thus, as a rule, the reactions are generally carried out homogeneously.

The catalysts used in our invention may best be defined as metal coordination complexes having the following general structure:

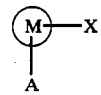

wherein M is or chromium, A is an anion such as $Cl^-$, $Br^-$, CN, $N^-_3$, $N^{-3}$, SCN, OCN, ON, OMe, chlorate, carboxylate such as acetate, propionate or benzoate, and the component depicted as "◯" is a porphyrin ligand as described below which additionally contains a halogen moiety, X. Preferably the anion is chloride, nitride, azide, or hydroxy.

The term "ligand" is used herein in its conventional meaning and refers generically to a group or system of atoms which forms one or more bonds to a metal ion, i.e., forms a coordination complex, and stabilizes this metal coordination complex in desirable oxidation states. Suitable ligands for the present purpose are the porphyrins (sometimes referred to as porphyrinatos) such as alkyl and aryl porphyrins such as tetraphenylporphyrins, octaethylporphyrins, tetramethylporphyrins and the like. Usually there are 0–8 substitutents, alkyl or aryl, on the basic porphyrin structure, the alkyls are $C_1$–$C_4$ and the aryls contain 1 or 2 rings which may themselves have alkyl substituents.

It is known to fluorinate metal coordination complex catalysts to improve their stability in the oxidation of alkanes and alkenes using strong oxidizers such as iodosyl benzene (C. Chang and F. Ebina, J. Chem. Comm. 778 (1981), but it has not been known for the oxidation of alkanes and alkenes with air or oxygen. However, we have additionally and unexpectedly found greatly increased catalyst selectivity to MEK from butane peculiar to the chromium porphyrin coordination complex, as described above, when the ligand is halogenated.

The halogen component, X, can be fluoride, chloride, bromide, iodide or mixtures thereof but preferably is one of the first three mentioned, more preferably fluoride. The degree of ligand halogenation should obviously be sufficient to improve the activity of the catalyst. Usually at least 15% of the replaceable hydrogen atoms of the ligand will be replaced by halogen, preferably at least 50%, more preferably at least 90%. The latter case is referred to herein as perhalogenation for which the conventional symbols are $F^-$, Cl, etc.

The catalysts used in our invention can be readily prepared by simple modifications of procedures described in the art for preparing unhalogenated ligands. For example, the unhalogenated Cr(TPP)Cl complex (in which "TPP" is tetraphenylporphyrinato) can be prepared by a standard method in which $(TPP)H_2$ and chromium (II) chloride are refluxed together in a dimethylformamide solution. Purification is achieved by chromatography. (See, e.g., A. D. Adler et al, *J. Inorg. Nucl. Chem.*, 32, 2443 (1970).) From these metal salts other anions such as the corresponding azides or hydroxides may be prepared by methathesis reactions with dissolved $NaN_3$ or hydrazoic acid or, for the hydroxide, potassium hydroxide.

To prepare the corresponding halogenated ligand coordination complex of this invention, one or more of the precursors of the ligand are halogenated before the ligand itself is produced by a condensation reaction. Thus, partially or fully fluorinated benzaldehyde is condensed with pyrrole yielding $(TPFPP)H_2$ (in which "(TPFPP)" is tetrakispentafluorophenylporphyrinato, one of the possible fluorination products of TPP, ranging from monofluorinated to perfluorinated TPP). Substituting this $(TPFPP)H_2$ for $(TPP)H_2$ in the aforementioned method of refluxinq in a dimethylformamide solution containing the Cr(II) salt will yield the corresponding Cr(TPFPP) salt.

By way of further illustration, Cr(TPFPP)Cl precursor is made as follows: 0.955 g of $H_2(TPFPP)$ and 2.20 g of $Cr(CO)_6$ is dissolved in 200 ml of $N_2$ degassed DMF and refluxed for 10 hours or until all of the free porphyrin has reacted according to the UV spectrum. The DMF is removed by vacuum distillation and the residue is taken up in $CHCl_3$ and filtered and washed with $H_2O$. The solids were dissolved in 50 ml $CHCl_3$, washed 3 times with 25 cc $H_2O$, separated and dried over $Na_2SO_4$. This $CHCl_3$ solution is chromatographed on dry basic alumina (activity II). The third band of dark green material is collected and rotovapped to dryness. Yield is 0.48 g after drying in vacuum overnight at 100°.

Azides and nitrides are made from this precursor as follows: 400 mg of Cr (TPFPP)Cl is dissolved in 100 ml of acetone. 4.0 g of $NaN_3$ is added and the mixture is stirred overnight at room temperature. After the solvent is removed and the solid product is washed with $H_2O$ and dried, a yield of 350 mg of $Cr(TPFPP)N_3$ is obtained. IR(KBr) shows a N—N stretch at 2053 $cm^{-1}$.

100 mg of $Cr(TPFP)N_3$ is dissolved in 100 ml of degassed THF and photolyzed at room temperature for 2 hours. The THF solution is rotovapped to dryness and the residue dissolved in a minimum of toluene and chromatographed on a $10'' \times 1''$ silica gel column. A single red band is collected, evaporated and vacuum dried at 100° to produce 60 mg of product. The IR reveals a 1017 $cm^{-1}$ shoulder on the 1010 $cm^{-1}$ porphyrin band which is the Cr≡N stretch comparable to 1021 $cm^{-1}$ in Cr(TPP)N. There is no evidence in the IR of any remaining azide.

The perhalogenated metal porphyrin $[Cr(TPFPP)Br_8]Cl$, chromium (tetrakispentafluorophenyloctabromoporphyrin) chloride is prepared as follows: Under $N_2$, a flask is charged with 1.0 g of Zn(TPFP), 1.85 g of N-bromosuccinimide, 0.25 g of benzoyl peroxide and 150 ml of $CCl_4$. This mixture is refluxed under $N_2$ for 5 hours and is then allowed to cool to room temperature. After chromatography on basic alumina, 300 mg. of pure $Zn(TPFPBr_8)$ is obtained and characterized by UV/VIS, IR and elemental analysis. The zinc is removed by acid treatment and the chromium complex $Cr(TPFPPBr_8)Cl$ is prepared by $CrCl_2$ and the chromium complex $Cr(TPFPPBr_8)Cl$ is prepared by $CrCl_2$ treatment in refluxing DMF. The azide, $Cr(TPFPPBr_8)N_3$, can be prepared by reaction of the chloride salt with $NaN_3$ in acetone. The hydroxo salt $Cr(TPFPBr_8)OH$ is prepared from the chloro salt by treatment with KOH in $CH_2Cl_2/H_2O$.

The perhalogenated metal porphyrin $Cr(TPFPPCl_8)Cl$ is prepared as follows: under $N_2$, 0.5 g of Zn dissolved in 5000 ml of $CCL_4$ is refluxed for 5 hr. while $Cl_2$ gas is bubbled slowly thorough the solution. After cooling the mixture is filtered and chromatographed on alumina, yielding 0.4 g of pure Zn $(TPFPPCl_8)$. The zinc is removed by trifluoroacetic acid treatment, and the chromium is then inserted by reaction with $CrCl_2$ in DMF. The resulting $Cr(TPFPPCl_8)Cl$ is characterized by UV/VIS, IR, and elemental analysis. Azide salts are prepared from the chloride salts by methathesis with $NaN_3$ in acetone. The hydroxo salt, $Cr(TPFPPCl_8)OH$, is prepared from the chloro salt by treatment with aqueous KOH solution in $CH_2Cl_2$.

The perfluorinated metal porphyrin, chromium, perfluorotetraphenylporphyrin chloride, Cr(FTPP)Cl (28 F atoms), can be prepared by the reaction of dilute $F_2$ gas in $N_2$ with Zn(TPFP) in $CCl_4$, with small added amounts of $CoF_3$ or $AgF_2$, followed by removal of zinc and incorporation of chromium as before. This porphyrin complex is analyzed by IR, UV/VIS, and elemental analysis. The azide salt is prepared from the chloride salt by reaction with $NaN_3$ in acetone. The hydroxo salt, Cr(FTPP)OH is prepared by the aqueous KOH treatment of the chloro salt in $CH_2Cl_2$.

The preparation of the following chromium complexes are examples of other porphyrins useable in our invention.

Freshly distilled pyrrole (0.8 g) and trifluoroacetaldehyde (10.9 g) are reflexed for 24 hr. in 500 ml of ethanol containing 10 ml of 48% HBr. After neutralization of the mixture and extraction of the crude tetrakis (trifluoromethyl)porphyrin into $CH_2Cl_2$, the $H_2(TTFMP)$ is purified by chromatography on alumina. Chromium is inserted into the $H_2(TTFMP)$ by normal $CrCl_2/DMF$ treatment giving Cr(TTFMP)Cl. The azide and hyroxide complexes are prepared by metathesis with $NaN_3$ in acetone and aqueous KOH in $CH_2Cl_2$ respectively. The pyrrolic hydrogens of this porphyrin can be partially or fully halogenated with Br, Cl, or F using the same techniques used for the tetraphenylporphyrins. As an example, dilute $F_2$ gas treatment of Zn(TTFMP) in the presence of $CoF_3$ in $CCl_4$ leads to isolation of the perfluorinated zinc porphyrin, Zn(FTMP). Removal of the zinc by strong acid treatment leads to the metal-free $H_2(FTMP)$ from which the chromium complex, Cr(FTMP)Cl can be prepared by $CrCl_2/DMF$ treatment. The azide, hydroxide, and nitride complexes are prepared in similar fashion to those described before.

Other chromium metal halogenated porphyrin salts are made analagously to the above methods. Similarly, when other porphyrin compounds are used similar results are obtained. The excellent selectivity of our catalysts depends on the porphyrin macro structure itself, not on any specific substituent group.

From the foregoing, it will be seen that our novel catalysts are comprised of three component parts: the porphyrin ligand moiety, which has been partially or fully halogenated, the chromium metal center which is bound to (i.e., complexed with) the ligand, and an anion, which is bound to the chromium. The metal-ligand portion is also frequently described in the art as a metal coordination complex.

The invention will now be illustrated by examples.

In each case, the complex was charged to a glass-lined autoclave and 48 mls of solvent added. 1 mole of n-butane was then pumped into the autoclave and the reaction mixture heated with stirring to the designated temperature. After stirring for the designated time period, the reactor was cooled and the gas and liquid contents analyzed. Very small amounts of $CO_2$ were present in the gas phase. Over 90% of the products were present in the liquid phase; In the table MEK=Methyl Ethyl Ketone, SBA -Sec Butyl Alcohol, AA=Acetic Acid+Acetic Anhydride (usually in about a 9/1 ratio). The catalyst, Cr(HFAA), is chromiumhexafluoroacetylacetonate, a control. N/A means not available. Under solvent, B=benzene and BN is benzonitrite. Selectivity is the amount if MEK formed relative to the total amount of MEK, SBA and AA.

TABLE I

| Example | Catalyst-mmoles | Solvent | Temp C | Hrs. | Product (mmoles) MEK | SBA | AA | MEK Selec. |
|---|---|---|---|---|---|---|---|---|
| 1 | Cr(HFAA) - .023 | B | 125 | 4.5 | 0 | 0 | 0 | — |
| 2 | Cr(TPFPP)Cl - .023 | B | 125 | 4.5 | 6.7 | 0.2 | 5.27 | 70 |
| 3 | Cr(TPFPP)Cl - .023 | B | 125 | 6.0 | 10.9 | 0.9 | 9.88 | 65 |
| 4 | Cr(TPFPP)Cl - .023 | BN | 125 | 4.25 | 8.8 | 0.6 | N/A | N/A |
| 5 | Cr(TPFPP)Cl - .023 | BN | 125 | 4.25 | 1.5 | N/A | N/A | N/A |
| 6 | Cr(TPFPP)Cl - .023 | B | 100 | 20 | 0 | 0 | 0 | — |
| 7 | Cr(TPFPP)N$_3$ - .023 | B | 125 | 4.5 | 4.2 | N/A | N/A | N/A |
| 8 | Cr(TPFPP)N$_3$ - .023 | B | 125 | 20 | 21.8 | 2.3 | 16.7 | 67 |
| 9 | Cr(TPFPP)N$_3$ - .023 | B | 150 | 3.0 | 11.6 | 1.1 | 8.4 | 68 |
| 10 | Cr(TPFPP)OH - .023 | B | 125 | 4.5 | 7.8 | 0.6 | 4.6 | 73 |
| 11 | Cr(TPFPP)OH - .023 | B | 125 | 22 | 14.8 | 1.8 | 9.3 | 69 |

From the foregoing results in Table I, it will be seen that selectivities of 65% and higher are obtained in our process.

What we claim is:

1. A process for the selective oxidation of butane which comprises contacting butane with air or oxygen in the presence of a coordination complex catalyst of the formula

wherein Cr is chromium; A is an anion; the component " " is a porhyrin ligand, and X is a halogen substituent of the ligand.

2. Process according to claim 1 wherein X is fluorine.

3. Process according to claim 1 wherein the ligand is a fluorinated tetraphenyl porphyrin.

4. Process according to claim 1 wherein A is $Cl^-$, $OIH^-$, $N_3$ or $N^{-3}$.

5. Process according to claim 1 wherein the butane selectivity is at least 65%.

* * * * *